United States Patent
Zhang et al.

(10) Patent No.: US 10,011,781 B2
(45) Date of Patent: Jul. 3, 2018

(54) METHODS OF REDUCING PHOSPHORUS CONTENT IN LIQUID HYDROCARBONS

(71) Applicant: Lyondell Chemical Technology, L.P., Houston, TX (US)

(72) Inventors: Lei Zhang, League City, TX (US); Daniel F. White, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/802,773

(22) Filed: Nov. 3, 2017

(65) Prior Publication Data

US 2018/0127662 A1 May 10, 2018

Related U.S. Application Data

(60) Provisional application No. 62/417,777, filed on Nov. 4, 2016.

(51) Int. Cl.
*C10G 29/16* (2006.01)

(52) U.S. Cl.
CPC ....... *C10G 29/16* (2013.01); *C10G 2300/202* (2013.01); *C10G 2400/22* (2013.01)

(58) Field of Classification Search
None
See application file for complete search history.

(56) References Cited

U.S. PATENT DOCUMENTS

| | | |
|---|---|---|
| 3,482,001 A | 12/1969 | Eberhardt |
| 3,709,953 A | 1/1973 | Bergem et al. |
| 6,492,568 B1 * | 12/2002 | Murray ............... C07C 7/14841 |
| | | 568/909 |
| 2003/0149313 A1 * | 8/2003 | Murray .................... C07C 2/12 |
| | | 568/910 |

* cited by examiner

*Primary Examiner* — Tam M Nguyen

(57) ABSTRACT

Provided herein are methods of reducing phosphorus content of a liquid hydrocarbon. The liquid hydrocarbon may be contacted with a catalyst that includes copper (II) oxide to produce a low-phosphorus liquid hydrocarbon.

17 Claims, No Drawings

METHODS OF REDUCING PHOSPHORUS CONTENT IN LIQUID HYDROCARBONS

CROSS-REFERENCE TO RELATED APPLICATIONS

This application claims the benefit of priority to U.S. Provisional Application No. 62/417,777 filed on Nov. 4, 2016, which is incorporated herein by reference in its entirety.

BACKGROUND

The removal of phosphorus containing compounds from liquid hydrocarbons and fractions that are used to make hydrocarbon fuels, such as kerosene, gasoline, jet fuel, diesel, etc., is often necessary to meet certain requirements.

Hydrocarbon effluent from a propylene metathesis production process or olefin conversion technology is one of the feedstocks that may be blended together with other hydrocarbon fractions to make other products, such as gasoline.

Hydrocarbon effluent from these processes may be a byproduct of a butenes-producing process that relies on the dimerization of ethylene. When catalysts using phosphorus-based ligands are used in the butenes-producing process, the resulting liquid hydrocarbon may contain phosphorus compounds, for example, as free ligands. In some instances, the presence of these phosphorus compounds may make the liquid hydrocarbon less suitable for blending into gasoline or other products.

For example, ethylene dimerization reactions typically utilize a catalyst to produce butenes, along with higher molecular weight hydrocarbon byproducts and catalyst decomposition products to form a liquid hydrocarbon, as shown in the following scheme:

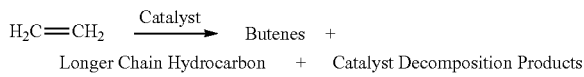

When the reaction is undergoing this dimerization of ethylene into butene, at least a portion of the catalyst decomposition byproducts may remain soluble in the reaction mixture. As a result, the liquid hydrocarbons, which may include longer chain hydrocarbon byproducts, may contain relatively high levels of phosphorus after separation. The presence of the phosphorus at certain levels can be disadvantageous, because if the liquid hydrocarbon is added to gasoline, the phosphorus content of the gasoline mixture may exceed the pipeline specification limit of 0.0038 gram per gallon. Therefore, in order to allow the liquid hydrocarbon to be blended with gasoline in refinery processing, the phosphorus content of the byproduct should, in some instances, be below 35 wtppm. When this threshold is exceeded, the amount of the byproduct that can be added to the gasoline is reduced, which may negatively impact the economics of the process.

Processes for reducing the content of phosphorus containing compounds have been devised, including distillation and treatment with an oxidizing agent to convert the phosphorus containing compounds to oxides, a portion of which can be removed due to their higher water solubility. These processes, however, typically are expensive, time-consuming, multi-step, and/or high temperature procedures.

Methods for effectively and efficiently reducing the concentration of phosphorus in liquid hydrocarbons are therefore desirable.

BRIEF SUMMARY

Provided herein are methods of reducing the phosphorus content of liquid hydrocarbons. In embodiments, the methods comprise contacting a liquid hydrocarbon with a catalyst comprising copper (II) oxide to produce a low-phosphorus liquid hydrocarbon, wherein the copper (II) oxide is present in the catalyst in an amount of at least 30% by weight of the catalyst, and the liquid hydrocarbon comprises a C4-C30 alkene and a C2-C30 trialkylphosphine.

While multiple embodiments are disclosed herein, still other embodiments of the present disclosure will become apparent to those skilled in the art from the following detailed description. As will be apparent, the disclosure is capable of modifications in various obvious aspects, all without departing from the spirit and scope of the present disclosure. Accordingly, the detailed description is to be regarded as illustrative in nature and not restrictive.

DETAILED DESCRIPTION

Provided herein are methods of reducing the phosphorus content of liquid hydrocarbons that may be performed at room temperature and ambient pressure. Also, in embodiments, the methods provided herein may be performed in a single step.

In embodiments, the methods comprise contacting a liquid hydrocarbon with a catalyst comprising copper (II) oxide to produce a low-phosphorus liquid hydrocarbon. The copper (II) oxide may be present in the catalyst in an amount of at least 30% by weight of the catalyst, and the liquid hydrocarbon may comprise a C4-C30 alkene and a C2-C30 trialkylphosphine.

The C2-C30 trialkylphosphine, in embodiments, is a decomposition product of a dimerization catalyst. In some embodiments, the C2-C30 trialkylphosphine is tri-n-butyl-phosphine (PBu$_3$), referred to herein simply as tributylphosphine. In further embodiments, the C2-C30 trialkylphosphine is tributylphosphine, and the tributylphosphine is a decomposition product of a dimerization catalyst.

As used herein, the phrase "concentration of phosphorus" or "phosphorus content" generally refers to the amount or concentration of elemental phosphorus in a sample, as calculated from gas chromatography (GC) data pertaining to phosphorus containing compounds. As used herein, the phrase "concentration of phosphorus containing compounds" or "phosphorus containing compounds content" generally refers to the amount or concentration of phosphorus containing compounds, such as tributylphosphine or tributylphosphine oxide, in a sample, as determined by GC.

In embodiments, the concentration of phosphorus in the liquid hydrocarbon is about 25 to about 100 wtppm, about 25 to about 75 wtppm, about 25 to about 50 wtppm, about 30 to about 50 wtppm, or about 30 to about 40 wtppm.

In embodiments, the concentration of phosphorus containing compounds in the liquid hydrocarbon is about 150 to about 700 wtppm, about 150 to about 500 wtppm, about 150 to about 350 wtppm, about 200 to about 350 wtppm, or about 200 to about 250 wtppm, where phosphorus containing compounds include tributylphosphine or tributylphosphine oxide.

As used herein, the phrase "low-phosphorus liquid hydrocarbon" refers to a liquid hydrocarbon that has been contacted with a catalyst comprising copper (II) oxide as provided herein. In embodiments, the phosphorus content of the low-phosphorus liquid hydrocarbon is about 0 to about 10 wtppm, about 0 to about 5 wtppm, about 0 to about 3 wtppm, about 1 to about 3 wtppm, or about 1 wtppm.

In embodiments, the phosphorus containing compounds content of the low-phosphorus liquid hydrocarbon is about 0 to about 65 wtppm, about 1 to about 30 wtppm, about 2 to about 20 wtppm, about 6 to about 20 wtppm, or about 6 wtppm.

In embodiments, the concentration of phosphorus in the liquid hydrocarbon is about 25 to about 100 wtppm, about 25 to about 75 wtppm, about 25 to about 50 wtppm, about 30 to about 50 wtppm, or about 30 to about 40 wtppm, and the concentration of phosphorus in the low-phosphorus liquid hydrocarbon is about 0 to about 10 wtppm.

In embodiments, the concentration of phosphorus in the liquid hydrocarbon is about 25 to about 100 wtppm, about 25 to about 75 wtppm, about 25 to about 50 wtppm, about 30 to about 50 wtppm, or about 30 to about 40 wtppm, and the concentration of phosphorus in the low-phosphorus liquid hydrocarbon is about 0 to about 5 wtppm.

In embodiments, the concentration of phosphorus in the liquid hydrocarbon is about 25 to about 100 wtppm, about 25 to about 75 wtppm, about 25 to about 50 wtppm, about 30 to about 50 wtppm, or about 30 to about 40 wtppm, and the concentration of phosphorus in the low-phosphorus liquid hydrocarbon is about 0 to about 3 wtppm.

In embodiments, the concentration of phosphorus in the liquid hydrocarbon is about 25 to about 100 wtppm, about 25 to about 75 wtppm, about 25 to about 50 wtppm, about 30 to about 50 wtppm, or about 30 to about 40 wtppm, and the concentration of phosphorus in the low-phosphorus liquid hydrocarbon is about 1 to about 3 wtppm.

In embodiments, the concentration of phosphorus in the liquid hydrocarbon is about 25 to about 100 wtppm, about 25 to about 75 wtppm, about 25 to about 50 wtppm, about 30 to about 50 wtppm, or about 30 to about 40 wtppm, and the concentration of phosphorus in the low-phosphorus liquid hydrocarbon is about 1 wtppm.

In embodiments, the concentration of phosphorus in the liquid hydrocarbon is about 25 to about 100 wtppm, and the phosphorus content of the low-phosphorus liquid hydrocarbon is about 0 to about 10 wtppm, about 0 to about 5 wtppm, about 0 to about 3 wtppm, about 1 to about 3 wtppm, or about 1 wtppm.

In embodiments, the concentration of phosphorus in the liquid hydrocarbon is about 25 to about 75 wtppm, and the phosphorus content of the low-phosphorus liquid hydrocarbon is about 0 to about 10 wtppm, about 0 to about 5 wtppm, about 0 to about 3 wtppm, about 1 to about 3 wtppm, or about 1 wtppm.

In embodiments, the concentration of phosphorus in the liquid hydrocarbon is about 25 to about 50 wtppm, and the phosphorus content of the low-phosphorus liquid hydrocarbon is about 0 to about 10 wtppm, about 0 to about 5 wtppm, about 0 to about 3 wtppm, about 1 to about 3 wtppm, or about 1 wtppm.

In embodiments, the concentration of phosphorus in the liquid hydrocarbon is about 30 to about 50 wtppm, and the phosphorus content of the low-phosphorus liquid hydrocarbon is about 0 to about 10 wtppm, about 0 to about 5 wtppm, about 0 to about 3 wtppm, about 1 to about 3 wtppm, or about 1 wtppm.

In embodiments, the concentration of phosphorus in the liquid hydrocarbon is about 30 to about 40 wtppm, and the phosphorus content of the low-phosphorus liquid hydrocarbon is about 0 to about 10 wtppm, about 0 to about 5 wtppm, about 0 to about 3 wtppm, about 1 to about 3 wtppm, or about 1 wtppm.

In embodiments, the concentration of phosphorus in the liquid hydrocarbon is at least 10, at least 15, at least 20, at least 25, at least 30, at least 35, or at least 40 times greater than the concentration of phosphorus in the low-phosphorus liquid hydrocarbon.

Liquid Hydrocarbons

Generally, the liquid hydrocarbons provided herein may comprise an alkene, a phosphine, a phosphine oxide, or a combination thereof. In one embodiment, the alkene is a C4-C30 alkene. In another embodiment, the phosphine is a C2-C30 trialkylphosphine. In a further embodiment, the phosphine oxide is a C2-C30 trialkylphosphine oxide. In a particular embodiment, the liquid hydrocarbon comprises a C4-C30 alkene and a C2-C30 trialkylphosphine. In a certain embodiment, the liquid hydrocarbon comprises a C4-C30 alkene, a C2-C30 trialkylphosphine, and a C2-C30 trialkylphosphine oxide. In another particular embodiment, the liquid hydrocarbon comprises a C4-C30 alkene, tributylphosphine (PBu$_3$), and tributylphosphine oxide.

In embodiments, the C4-C30 alkene of the liquid hydrocarbons provided herein comprises a C5 olefin, a C6 olefin, or a combination thereof. The C5 olefin, C6 olefin, or a combination thereof may be present in the liquid hydrocarbon in an amount of at least 50%, at least 60%, at least 70%, at least 80%, or at least 90% by weight of the liquid hydrocarbon. In one embodiment, the liquid hydrocarbon comprises a combination of C5 olefins and C6 olefins, wherein the combination of C5 olefins and C6 olefins is present in the liquid hydrocarbon in an amount of at least 50% by weight of the liquid hydrocarbon.

In embodiments, the liquid hydrocarbon is a reaction mixture, e.g., an outflow from a chemical manufacturing process. The chemical manufacturing process may be an ethylene dimerization reaction. As a result, in particular embodiments, the methods provided herein comprise producing the liquid hydrocarbon by contacting ethylene with a dimerization catalyst prior to contacting the liquid hydrocarbon and the catalyst provided herein. In a particular embodiment, $C_2$-$C_{30}$ trialkylphosphine, such as PBu$_3$, is a decomposition product of the dimerization catalyst. In further embodiments, the methods provided herein comprise contacting an outflow from an ethylene dimerization reaction with a catalyst to reduce the phosphorus content of the reaction mixture.

An ethylene dimerization reaction may produce butene, as disclosed, for example, by U.S. Pat. No. 3,482,001 and U.S. Pat. No. 3,709,953, which are incorporated herein by reference. In some embodiments, the resulting butene mixtures contain 1-butene and 2-butenes in the form of cis-2-butene and trans-2-butene. The process also produces catalytic decomposition products including nickel salt, aluminum salt, chloride, and phosphorus compounds. In some embodiments, the concentration of the catalytic decomposition products in the reaction byproduct is 1 to 200 wtppm nickel, 5 to 2000 wtppm aluminum, 10 to 500 wtppm chlorine, and 2 to 200 wtppm phosphorus.

In embodiments, when the liquid hydrocarbon is a butene reactor effluent, the hydrocarbon phase may be treated to separate the longer chain hydrocarbon material (e.g., hydrocarbons containing more than five carbons) from butene. In some embodiments, the reactor effluent in the hydrocarbon phase comprises about 75 to about 99 weight % butene. In further embodiments, the reactor effluent contains about 85 to about 98 weight % butene. In additional embodiments, the reactor effluent in the hydrocarbon phase further comprises about 1 to about 25 weight % longer chain hydrocarbon byproducts. In some embodiments, the reactor effluent comprises about 2 to about 15 weight % longer chain hydrocarbon byproducts. In some embodiments, the reactor effluent comprises about 10 weight % of the longer chain hydrocarbon byproducts.

In embodiments, the liquid hydrocarbon is a gasoline precursor. Therefore, in some embodiments, the methods provided herein comprise contacting a gasoline precursor or gasoline precursor stream with a catalyst provided herein in order to reduce the phosphorus content of the gasoline precursor or gasoline precursor stream. In one embodiment, the gasoline precursor stream is a mixture comprising butene dimerization reaction long chain hydrocarbon byproducts and/or other C5-C8 hydrocarbons. In a further embodiment, the methods provided herein comprise contacting the gasoline precursor or gasoline precursor stream after the butene and the ethylene components have been separated from the C5 and greater hydrocarbons. The hydrocarbon phase may be further processed to obtain gasoline or other refinery products.

Catalysts

The catalysts provided herein, which are used to reduce phosphorus content, generally comprise copper (II) oxide. In one embodiment, the catalyst consists of copper (II) oxide, i.e., the catalyst is copper (II) oxide. In a certain embodiment, the catalyst comprises copper (II) oxide in an amount of at least 30% by weight of the catalyst, or at least 40% by weight of the catalyst. In another embodiment, copper (II) oxide may be present in the catalysts in an amount of about 20 to about 99% by weight of the catalyst, about 20 to about 90% by weight of the catalyst, about 20 to about 80% by weight of the catalyst, about 20 to about 70% by weight of the catalyst, about 20 to about 60% by weight of the catalyst, about 20 to about 50% by weight of the catalyst, about 30 to about 50% by weight of the catalyst, or about 40% by weight of the catalyst. As used herein, the term "catalyst" refers to the material that is or comprises copper (II) oxide.

In embodiments, the catalyst comprises copper (II) oxide and at least one of zinc oxide and aluminum oxide.

In embodiments, the catalyst comprises copper (II) oxide and zinc oxide. In one embodiment, copper (II) oxide may be present in the catalysts in an amount of about 20 to about 99% by weight of the catalyst, and the zinc oxide may be present in an amount of about 1 to about 80% by weight of the catalyst. In another embodiment, copper (II) oxide may be present in the catalysts in an amount of about 20 to about 90% by weight of the catalyst, and the zinc oxide may be present in an amount of about 10 to about 80% by weight of the catalyst. In a further embodiment, copper (II) oxide may be present in the catalysts in an amount of about 20 to about 80% by weight of the catalyst, and the zinc oxide may be present in an amount of about 20 to about 80% by weight of the catalyst. In an additional embodiment, copper (II) oxide may be present in the catalysts in an amount of about 20 to about 70% by weight of the catalyst, and the zinc oxide may be present in an amount of about 30 to about 80% by weight of the catalyst. In yet another embodiment, copper (II) oxide may be present in the catalysts in an amount of about 20 to about 60% by weight of the catalyst, and the zinc oxide may be present in an amount of about 40 to about 80% by weight of the catalyst. In a still further embodiment, copper (II) oxide may be present in the catalysts in an amount of about 20 to about 50% by weight of the catalyst, and the zinc oxide may be present in an amount of about 50 to about 80% by weight of the catalyst. In yet another further embodiment, copper (II) oxide may be present in the catalysts in an amount of about 30 to about 50% by weight of the catalyst, and the zinc oxide may be present in an amount of about 50 to about 70% by weight of the catalyst. In yet another further embodiment, copper (II) oxide may be present in the catalysts in an amount of about 40% by weight of the catalyst, and the zinc oxide may be present in an amount of about 60% by weight of the catalyst.

In embodiments, the catalyst comprises copper (II) oxide and aluminum oxide. In one embodiment, copper (II) oxide may be present in the catalysts in an amount of about 20 to about 99% by weight of the catalyst, and the aluminum oxide may be present in an amount of about 1 to about 80% by weight of the catalyst. In another embodiment, copper (II) oxide may be present in the catalysts in an amount of about 20 to about 90% by weight of the catalyst, and the aluminum oxide may be present in an amount of about 10 to about 80% by weight of the catalyst. In a further embodiment, copper (II) oxide may be present in the catalysts in an amount of about 20 to about 80% by weight of the catalyst, and the aluminum oxide may be present in an amount of about 20 to about 80% by weight of the catalyst. In an additional embodiment, copper (II) oxide may be present in the catalysts in an amount of about 20 to about 70% by weight of the catalyst, and the aluminum oxide may be present in an amount of about 30 to about 80% by weight of the catalyst. In yet another embodiment, copper (II) oxide may be present in the catalysts in an amount of about 20 to about 60% by weight of the catalyst, and the aluminum oxide may be present in an amount of about 40 to about 80% by weight of the catalyst. In a still further embodiment, copper (II) oxide may be present in the catalysts in an amount of about 20 to about 50% by weight of the catalyst, and the aluminum oxide may be present in an amount of about 50 to about 80% by weight of the catalyst. In yet another further embodiment, copper (II) oxide may be present in the catalysts in an amount of about 30 to about 50% by weight of the catalyst, and the aluminum oxide may be present in an amount of about 50 to about 70% by weight of the catalyst. In yet another further embodiment, copper (II) oxide may be present in the catalysts in an amount of about 40% by weight of the catalyst, and the aluminum oxide may be present in an amount of about 60% by weight of the catalyst.

In embodiments, the catalyst comprises copper (II) oxide, zinc oxide, and aluminum oxide. In one embodiment, the copper (II) oxide is present in the catalyst in an amount of about 20 to about 60% by weight of the catalyst, the zinc oxide is present in the catalyst in an amount of about 20 to about 60% by weight of the catalyst, and the aluminum oxide is present in the catalyst in an amount of about 1 to about 40% by weight of the catalyst. In another embodiment, the copper (II) oxide is present in the catalyst in an amount of about 30 to about 50% by weight of the catalyst, the zinc oxide is present in the catalyst in an amount of about 30 to about 50% by weight of the catalyst, and the aluminum oxide is present in the catalyst in an amount of about 10 to about 30% by weight of the catalyst. In a further embodiment, the copper (II) oxide is present in the catalyst in an amount of about 35 to about 45% by weight of the catalyst, the zinc oxide is present in the catalyst in an amount of about 35 to about 45% by weight of the catalyst, and the aluminum oxide is present in the catalyst in an amount of about 15 to about 25% by weight of the catalyst. In an additional embodiment, the copper (II) oxide is present in the catalyst in an amount of about 40% by weight of the catalyst, the zinc oxide is present in the catalyst in an amount of 40% by weight of the catalyst, and the aluminum oxide is present in the catalyst in an amount of about 20% by weight of the catalyst.

In embodiments, the catalyst is a particulate material. In one embodiment, the copper (II) oxide is a particulate material. The particulate material may have an average particle diameter, as measured by X-ray diffraction (XRD), of about 25 µm to about 500 µm, about 50 µm to about 400 µm, about 100 to about 300 µm, or about 150 to about 250 µm.

In embodiments, the catalyst is a particulate material that is formed into a shape, such as a tablet or other shape suitable for a catalyst bed. The tablets may be of any size or have any dimensions. In one embodiment, the tablet is about 3 mm by about 3 mm.

In embodiments, the catalyst has a bulk density of at least 1000 kg/m$^3$. In one embodiment, the catalyst has a bulk density of about 1000 to about 1500 kg/m$^3$. In another embodiment, the catalyst has a bulk density of about 1100 to about 1400 kg/m$^3$. In a further embodiment, the catalyst has a bulk density of about 1200 to about 1300 kg/m$^3$. In an additional embodiment, the catalyst has a bulk density of about 1250 kg/m$^3$.

In embodiments, the catalyst has an operating temperature of about 15 to about 250° C. Therefore, in one embodiment, the methods provided herein or one or more steps thereof, which include contacting a liquid hydrocarbon with a catalyst, occur at a temperature of about 15 ° C. to about 250° C., about 15° C. to about 200° C., about 15° C. to about 150° C., about 15° C. to about 100° C., about 15° C. to about 75° C., about 15° C. to about 50° C., about 15° C. to about 40° C., about 15° C. to about 35° C., about 15° C. to about 25° C., or about 20° C. In a particular embodiment, the methods provided herein or one or more steps thereof, which include contacting a liquid hydrocarbon with a catalyst, occur at room temperature. In a further embodiment, the methods provided herein or one or more steps thereof, which include contacting a liquid hydrocarbon with a catalyst, occur at room temperature (around 25° C.) and ambient pressure.

In embodiments, the catalyst is disposed in a catalyst bed. In one embodiment, the methods provided herein or one or more steps thereof comprise contacting a liquid hydrocarbon with a catalyst by passing a stream of the liquid hydrocarbon through a catalyst bed.

In one embodiment, the catalyst is BASF® R3-12 copper (II) oxide catalyst.

Contacting a Liquid Hydrocarbon with a Catalyst

In the methods provided herein, a liquid hydrocarbon and a catalyst generally may be contacted by any means known in the art. In one embodiment, the catalyst and liquid hydrocarbon are contacted in a vessel. Agitation of any kind, including stirring, may be used. In another embodiment, the liquid hydrocarbon may be a stream that contacts the catalyst.

Generally, any weight ratio of liquid hydrocarbon to catalyst may be used that is capable of reducing the phosphorus content of the liquid hydrocarbon to a desirable level. In one embodiment, the weight ratio of liquid hydrocarbon to catalyst is about 100:10 to about 100:0.5, about 100:10 to about 100:1, about 100:8 to about 100:1, about 100:6 to about 100:1, about 100:6 to about 100:2, about 100:4 to about 100:3, about 100:4, or about 100:3.

Applications of Low Phosphorus Liquid Hydrocarbons

In embodiments, the liquid hydrocarbon which has been contacted with the catalyst is a gasoline precursor which may be further processed to obtain a commercially useful gasoline. The gasoline precursor, which can include C5 and greater hydrocarbons, may be admixed with one or more other sources of gasoline quality hydrocarbons to obtain a gasoline product which is acceptable for commercial sale. In some embodiments, the gasoline precursor is subjected to further alkylation reactions to increase the alkyl length of the material before formulation into gasoline.

The methods provided herein can be further modified and optimized for preparative, pilot- or large-scale production, either batch or continuous, using the principles and techniques of process chemistry as applied by a person skilled in the art. Such principles and techniques are taught, for example, in Practical Process Research & Development (2012), which is incorporated by reference herein.

Definitions

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, i-butyl, t-Bu or ⅔u), and —CH$_2$C(CH$_3$)$_3$ (neo-pentyl) are non-limiting examples of alkyl groups. The term "alkane" is a group of the formula: R—H, wherein R is an alkyl group.

The terms "phosphine" and "phosphane" are used synonymously herein. When used without the "substituted" modifier these terms refer to a compound of the formula PR$_3$, wherein each R is independently hydrogen, alkyl, cycloalkyl, alkenyl, aryl, or aralkyl, as those terms are defined above. The terms "trialkylphosphine" and "trialkylphosphane" are also synonymous. Such groups are a subset of phosphine, wherein each R is an alkyl group.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkane" is a group of the formula: R—H, wherein R is a cycloalkyl group.

The term "alkenyl" when used without the "substituted" modifier refers to an monovalent unsaturated aliphatic group with a carbon atom as the point of attachment, a linear or branched acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkene" is a group of the formula: R—H, wherein R is an alkenyl group.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "phosphine oxide" when used without the "substituted" modifier refers to a compound of the formula OPR$_3$, wherein each R is independently hydrogen, alkyl, cycloalkyl, alkenyl, aryl, or aralkyl, as those terms are defined above. Non-limiting examples include OPMe$_3$ (trimethylphosphine oxide), OPBu$_3$ (tributylphosphine oxide), and PPh$_3$O (triphenylphosphine oxide).

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —$C_6H_4CH_2CH_3$ (ethylphenyl), naphthyl, and a monovalent group derived from biphenyl.

The phrase "phosphorus containing compounds" is used to refer to compounds containing one or more phosphorus atoms with the molecular formula. The term "phosphorus" when used in the context of a composition refers to a composition containing one or more phosphorus compounds as that term is defined above or elemental phosphorus. Alternatively, this term may also be used to reference to the concentration of phosphorus atoms in the composition.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes those within ±10% of the indicated number.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "gasoline" is used to describe a C5 or greater hydrocarbon containing composition which has been prepared for use as a fuel source in an internal combustion engine. The term "gasoline precursor" refers to a composition which contains C5 or greater hydrocarbons that is added to other hydrocarbon material to obtain gasoline.

The term "hydrocarbon" is used to refer to a composition of organic compounds contain one or more carbon atoms and comprises at least 90% molecules with only carbon and hydrogen. The term "liquid hydrocarbon" and "hydrocarbon by-product" are used interchangeably to refer to a composition containing multiple different aliphatic, aromatic, or both compounds from a composition arising from the production of butene or other higher carbon length products such as gasoline. The term "hydrocarbon effluent" or "reactor effluent" is a subset of liquid hydrocarbon wherein the liquid hydrocarbon is from a chemical process, such as an ethylene dimerization process to produce butene, and may contain C5 or longer hydrocarbons.

A "method" is series of one or more steps undertaking lead to a final product, result or outcome. As used herein, the word "method" is used interchangeably with the word "process".

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1

Comparison of Adsorbents/Catalysts

Two materials (one adsorbent and one catalyst) were tested to determine their ability to reduce the phosphorus content of a liquid hydrocarbon. The liquid hydrocarbon used in this example was a sample containing a majority of C5 and C6 olefins. The C5 and C6 olefins, in other words, were present in the liquid hydrocarbon in an amount of at least 50% by weight of the liquid hydrocarbon.

The liquid hydrocarbon of this example was analyzed using GC. GC analysis, as shown at Table 1 below, revealed that the liquid hydrocarbon of this example included 35 wtppm of elemental phosphorus, which came from 202 wtppm of tributylphosphine, and 31 wtppm of tributylphosphine oxide. X-ray fluorescent (XRF) analysis revealed that the liquid hydrocarbon of this example included 40.5 wtppm of elemental phosphorus.

The liquid hydrocarbon of this example was contacted with two materials—(1) charcoal (an adsorbent), and (2) R3-12 Arsine Treater Catalyst (BASF®, Germany)—according to the following procedure. To a 100 mL round bottom flask, about 1.00 g of adsorbent/catalyst and about 40 mL of the liquid hydrocarbon of this example were added. The mixture was stirred at room temperature for 30 minutes at 600 RPM with a magnetic stirrer. The supernatant, after solid settling, was then tested by GC and XRF, and the results are provided in the following table.

TABLE 1

GC and XRF Data for Liquid Hydrocarbon of Example 1

| Sample | LH (mL) | LH (g) | Ad./Cat. (g) | LH/Ad. % or LH/Cat. % | P (wtppm) (GC) | TBP (wtppm) (GC) | TBPO (wtppm) (GC) | P (wtppm) (XRF) |
|---|---|---|---|---|---|---|---|---|
| 1 (LH) | | | | | 35 | 202 | 31 | 40.5 |
| 2 (LH & Charcoal) | 40 | 25.849 | 0.955 | 3.69 | 4 | 8 | 21 | <5 |

TABLE 1-continued

GC and XRF Data for Liquid Hydrocarbon of Example 1

| Sample | LH (mL) | LH (g) | Ad./Cat. (g) | LH/Ad. % or LH/Cat. % | P (wtppm) (GC) | TBP (wtppm) (GC) | TBPO (wtppm) (GC) | P (wtppm) (XRF) |
|---|---|---|---|---|---|---|---|---|
| 3 (LH & R3-12) | 40 | 25.832 | 1.129 | 4.37 | 1 | NA | 4 | <5 |

("Ad./Cat."—Adsorbent/Catalyst; "LH"—liquid hydrocarbon of Example 1; "TBP"—tributylphosphine; "TBPO"—tributylphosphine oxide)

The data of Table 1 demonstrated that treatment of the liquid hydrocarbon of Example 1 with R3-12 Arsine Treater Catalyst significantly reduced the content of elemental phosphorus, tributylphosphine, and tributylphosphine oxide in the liquid hydrocarbon.

We claim:

1. A method of reducing phosphorus content, the method comprising:
   contacting a liquid hydrocarbon with a catalyst comprising copper (II) oxide to produce a low-phosphorus liquid hydrocarbon,
   wherein the copper (II) oxide is present in the catalyst in an amount of at least 30% by weight of the catalyst, and the liquid hydrocarbon comprises a C4-C30 alkene and a C2-C30 trialkylphosphine.

2. The method of claim 1, wherein the C2-C30 trialkylphosphine is tributylphosphine ($PBu_3$).

3. The method of claim 1, wherein the concentration of phosphorus in the liquid hydrocarbon is about 25 to about 100 wtppm, and the concentration of phosphorus in the low-phosphorus liquid hydrocarbon is about 0 to about 10 wtppm.

4. The method of claim 1, wherein the concentration of phosphorus in the liquid hydrocarbon is about 30 to about 50 wtppm, and the concentration of phosphorus in the low-phosphorus liquid hydrocarbon is about 0 to about 3 wtppm.

5. The method of claim 1, wherein the concentration of phosphorus in the liquid hydrocarbon is at least 20 times greater than the concentration of phosphorus in the low-phosphorus liquid hydrocarbon.

6. The method of claim 1, wherein the concentration of phosphorus in the liquid hydrocarbon is at least 35 times greater than the concentration of phosphorus in the low-phosphorus liquid hydrocarbon.

7. The method of claim 1, wherein the catalyst is disposed in a catalyst bed, and contacting the liquid hydrocarbon with the catalyst comprises passing a stream of the liquid hydrocarbon through the catalyst bed.

8. The method of claim 1, wherein the copper (II) oxide is present in the catalyst in an amount of about 40% by weight of the catalyst.

9. The method of claim 1, wherein the catalyst is a particulate material having an average particle diameter of about 25 µm to about 500 µm.

10. The method of claim 1, wherein the catalyst further comprises at least one of zinc oxide and aluminum oxide.

11. The method of claim 10, wherein the copper (II) oxide is present in the catalyst in an amount of about 30 to about 50% by weight of the catalyst, the zinc oxide is present in the catalyst in an amount of about 30 to about 50% by weight of the catalyst, and the aluminum oxide is present in the catalyst in an amount of about 10 to about 30% by weight of the catalyst.

12. The method of claim 10, wherein the copper (II) oxide is present in the catalyst in an amount of about 40% by weight of the catalyst, the zinc oxide is present in the catalyst in an amount of 40% by weight of the catalyst, and the aluminum oxide is present in the catalyst in an amount of about 20% by weight of the catalyst.

13. The method of claim 1, wherein the liquid hydrocarbon comprises a combination of C5 olefins and C6 olefins, wherein the combination of C5 olefins and C6 olefins is present in the liquid hydrocarbon in an amount of at least 50% by weight of the liquid hydrocarbon.

14. The method of claim 1, further comprising producing the liquid hydrocarbon by contacting ethylene with a dimerization catalyst prior to contacting the liquid hydrocarbon and the catalyst.

15. The method of claim 14, wherein the $C_2$-$C_{30}$ trialkylphosphine is a decomposition product of the dimerization catalyst.

16. The method of claim 1, wherein the catalyst is BASF® R3-12 copper (II) oxide catalyst.

17. The method of claim 1, wherein the contacting of the liquid hydrocarbon and the catalyst occurs at a temperature of about 15° C. to about 250° C.

* * * * *